US012678607B2

(12) United States Patent
Lim

(10) Patent No.: US 12,678,607 B2
(45) Date of Patent: Jul. 14, 2026

(54) PYRAMIDAL MICRONEEDLES WITH ENHANCED DRUG LOADING CAPACITY AND METHOD FOR MANUFACTURING

(71) Applicant: Chee Yen Lim, Singapore (SG)

(72) Inventor: Chee Yen Lim, Singapore (SG)

( * ) Notice: Subject to any disclaimer, the term of this patent is extended or adjusted under 35 U.S.C. 154(b) by 1035 days.

(21) Appl. No.: 17/812,447

(22) Filed: Jul. 14, 2022

(65) Prior Publication Data

US 2022/0362533 A1 Nov. 17, 2022

Related U.S. Application Data

(62) Division of application No. 16/500,139, filed as application No. PCT/SG2017/050243 on May 10, 2017, now Pat. No. 11,701,506.

(51) Int. Cl.
| | |
|---|---|
| *B29C 33/38* | (2006.01) |
| *A61K 9/00* | (2006.01) |
| *A61M 37/00* | (2006.01) |

(52) U.S. Cl.
CPC ....... *A61M 37/0015* (2013.01); *A61K 9/0021* (2013.01); *A61M 2037/0023* (2013.01);
(Continued)

(58) Field of Classification Search
CPC ..... B29C 33/3878; B29C 33/40; B29C 33/42; B29C 33/0805; B29C 43/36; B29C 43/56; B29C 43/021; A61M 2037/0053
See application file for complete search history.

(56) References Cited

U.S. PATENT DOCUMENTS

2012/0078189 A1 3/2012 Ogawa et al.
2018/0333899 A1* 11/2018 Francis ............... B29C 33/3857

FOREIGN PATENT DOCUMENTS

WO 2015164840 A1 10/2015

OTHER PUBLICATIONS

ISR; Austrian Patent Office; Jan. 17, 2018.

* cited by examiner

*Primary Examiner* — Thu Khanh T. Nguyen
(74) *Attorney, Agent, or Firm* — Patshegen IP; Moshe Pinchas

(57) ABSTRACT

The present invention provides a solution to increase the drug loading capacity and drug delivery precision of dissolving microneedles. These solutions include: (a) increasing the base of the microneedle cavities without substantially changing the microneedle's height and geometry, (b) use of drug suspension and (c) a specific centrifugation order for filling drug and matrix material. In the first preferred embodiment, a microneedle master mould comprising a plurality of microneedles, wherein each of the microneedles further comprising a chamfered base which extends to and adjoins with its neighboring chamfered bases is provided. In the second preferred embodiment, a method of making dissolving microneedles is provided, comprising (a) providing a microneedle template comprising a plurality of microneedle cavities, wherein each of the microneedle cavities further comprising a chamfered base which extends to and adjoins with its neighboring chamfered bases; (b) dispensing a drug suspension in the substrate cavity on the microneedle template; (c) centrifuging the microneedle template which is loaded with a drug suspension, (d) dispensing a matrix material solution in the substrate cavity on the microneedle template; (d) centrifuging the microneedle template loaded with the drug suspension and the matrix material solution; and (e) drying the centrifuged microneedle template in a controlled environment.

20 Claims, 7 Drawing Sheets

(52) U.S. Cl.
CPC ............... *A61M 2037/0046* (2013.01); *A61M 2037/0053* (2013.01); *B29C 33/3842* (2013.01); *B29C 33/3878* (2013.01)

4100

4000

5100

7100

7000

7200

7100

7000

7200

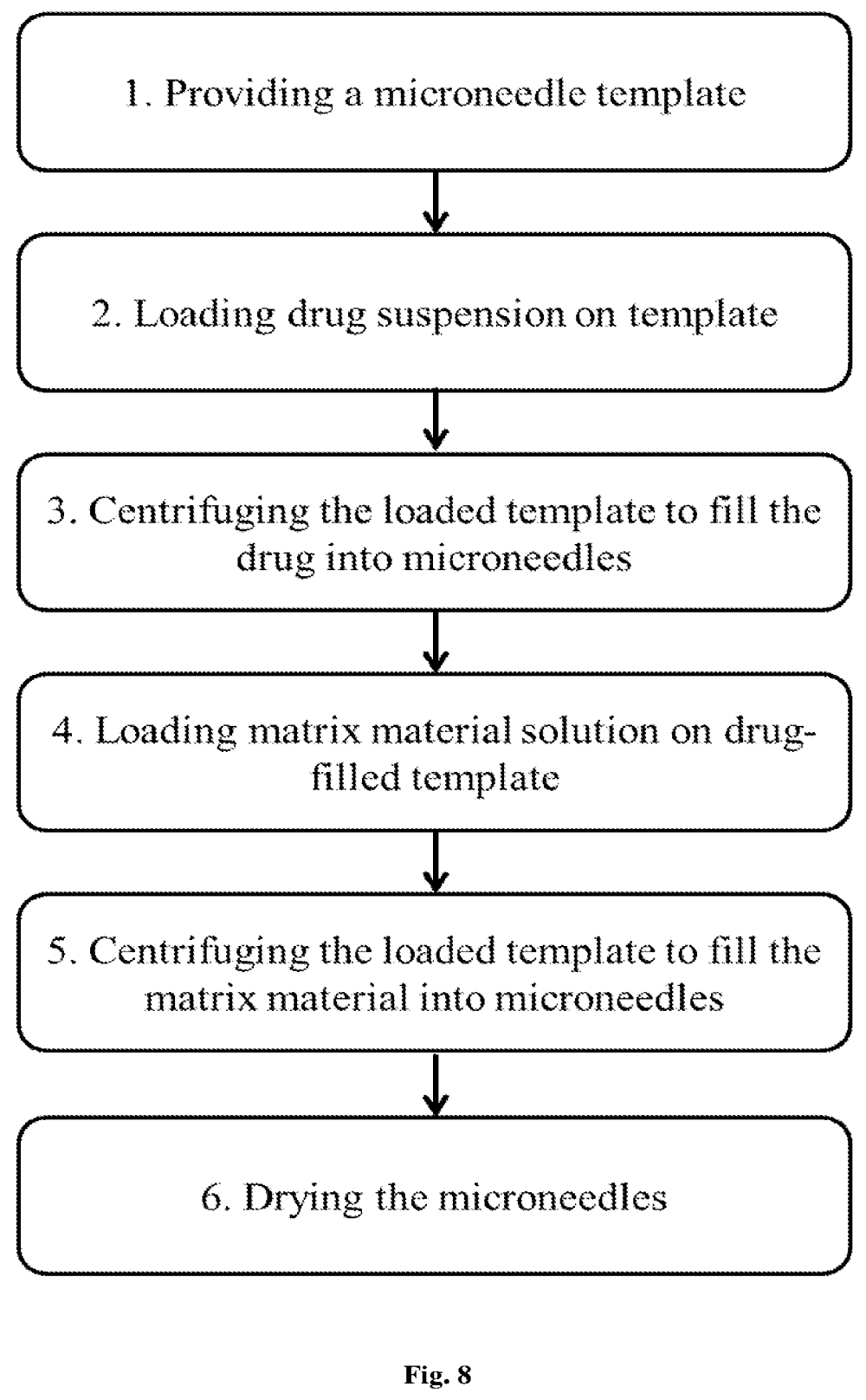

1. Providing a microneedle template

2. Loading drug suspension on template

3. Centrifuging the loaded template to fill the drug into microneedles

4. Loading matrix material solution on drug-filled template

5. Centrifuging the loaded template to fill the matrix material into microneedles 6. Drying the microneedles

Fig. 8

PYRAMIDAL MICRONEEDLES WITH ENHANCED DRUG LOADING CAPACITY AND METHOD FOR MANUFACTURING

FIELD OF THE INVENTION

The present invention relates to intradermal drug delivery using microneedles. More particularly, the present invention relates to methods of enhancing the drug loading capacity of microneedles.

BACKGROUND OF THE INVENTION

Microneedles are tiny spikes having submillimeter heights of 50 um-500 um that are normally loaded with drugs to be delivered into the skin painlessly. As the microneedles physically penetrate the skin, it is considered an intradermal route and is more effective than transdermal patches which do not physically penetrate the skin in delivering drugs to the skin. Microneedle patches are preferred in drug delivery for several beneficial features. For instance, compared with parenteral (injection with needles) administration, it is painless and therefore can be self-administered by the patients. Compared with oral administration, it is delivered directly to the systemic circulation without going through the gastro-intestinal tract. This means the delivered drugs circumvent the ingestion by the stomach and the first pass metabolism by the liver, and their dose as a result may be much lower for achieving the desirable therapeutic effect.

However, microneedle technology has its own limitations, namely in its drug loading capacity and delivery precision. The low capacity in drug loading is caused by the tiny surface or volume of the microneedles into which the drug can be loaded. Only the drug that is loaded on the microneedles which penetrate the skin will get delivered. On the other hand, the delivery precision is affected by the varying amount of drug loaded in the microneedles, and the varying (or incomplete) dissolution of the microneedles.

To increase the drug loading capacity, typically one increases the size of the microneedles (i.e. increase the height and base of the microneedles) or the number of the microneedles. However, increasing the size of microneedles may increase the pain caused by the microneedles and/or negatively affect the dissolution rate of microneedles. On the other hand, increasing the number of microneedles will inevitably increase the patch size causing ineffective skin penetration and therefore variable drug delivery. The first objective of the present invention aims to provide a solution to significantly increase the drug loading capacity of a microneedle patch while reducing the drug waste. The second objective of the present invention is to improve the drug delivery precision.

To increase the delivery precision and reduce drug wastage, PCT application WO2015/122838A1 proposed to employ centrifugal force to sediment the suspended insoluble particles to the bottom of the microneedle template. Although the centrifugation concentrated the drug at the tips of microneedles, which subsequently ensures the complete and repeatable drug delivery to the skin, this method only slightly increased the drug loading because the area of the substrate on which the drug sediments is much larger than the total base area of the microneedle cavities and majority of drug still lands on the substrate. It is clear that if the microneedles are made foot-to-foot, i.e. there is no substrate area in between two microneedles to collect the drug sediment, then all the drug sediment go to the tips of the microneedle cavities. This will significantly enhance the drug loading capacity of the microneedle patch.

To increase the delivery precision, the common practice is to perform multi-layer castings on the microneedle template so that the drug layer is disposed at the tips of the microneedles.

For example, U.S. Pat. No. 8,911,749B2 awarded to Corium proposed a multi-layered microneedle patch having the drug layer disposed at the tips of microneedles. However, this method is tedious because it involved several cycles of casting and drying, which may be impractical for mass production. For the drug to be precisely loaded into the microneedle cavities and not the substrate, direct dispensing of drug into individual microneedle cavities is required, which is impractical due to the requirement in ultra-high precision of positioning and volume control of the dispensing tip and the vast amount of dispensing that are involved in mass production.

Hence, there is a long-felt need in increasing the drug loading capacity and delivery precision of the dissolving microneedle patches.

SUMMARY OF THE INVENTION

The present invention relates to a method for increasing the drug loading capacity and the delivery precision. Using a drug suspension comprising 0.5%-5% solids by weight with particle size <5 um in diameter, the insoluble drug particles are pushed to the tips of the microneedles by a centrifugation process. As mentioned earlier, only a tiny fraction of the drug is normally loaded in the microneedles, because only the drug directly above the microneedle cavities will be pushed to the tips of microneedle cavities by the centrifugation process, and the area ratio of cavities to substrate is small.

The present invention proposes several solutions to enhance the drug loading capacity of a dissolving microneedle patch and its delivery precision. The first solution is to increase the area ratio of the microneedle cavities to the substrate to allow more drugs to get into the microneedles. The solution involves increasing the bases' area of the microneedle cavities without substantially changing the microneedle's height and geometry. The second solution is to avoid the viscoelastic property of the matrix material which arises when liquid flow involves micro-scale dimensions by filling the drug into the microneedle cavities first before filling the matrix material, allowing all drug particles to sediment to the tips of microneedles.

In a first preferred embodiment, a microneedle template comprising a plurality of microneedle cavities, wherein each of the microneedle cavities further comprising a chamfered base which extends to and adjoins with its neighboring chamfered bases is provided.

In the second preferred embodiment, a method of making dissolving microneedles is provided, comprising (a) providing a microneedle template comprising a plurality of microneedle cavities, wherein each of the microneedle cavities further comprising a chamfered base which extends to and adjoins with its neighboring chamfered bases; (b) loading a drug suspension in the substrate cavity on the microneedle template; (c) centrifuging the microneedle template which is loaded with a drug suspension, (d) loading a matrix material solution in the substrate cavity on the microneedle template; (d) centrifuging the microneedle template loaded with the drug suspension and the matrix material solution; and (e) drying the centrifuged microneedle template in a controlled environment.

BRIEF DESCRIPTION OF THE FIGURES

FIG. 8 shows a flow chart that summarizes the steps for making dissolving microneedles with enhanced drug loading capacity.

DETAILED DESCRIPTION OF THE INVENTION

Drugs may be insoluble and made in suspensions of 0.5%-5% solid weight. The suspensions normally have small particles (e.g. <5 um diameter) as solids dispersed in water. These insoluble solid particles will slowly sediment to the bottom when the suspension is left alone for some time. This sedimentation phenomenon can be used to concentrate the drug on the tips of microneedles as explained in the following paragraphs.

Microneedle patches suffer from very low drug loading capacity due to the size of the microneedles. For instance, a typical microneedle of 500 um height (H), 150 um base, pyramid shape, the volume is $\frac{1}{3}$ HB$^2$=3.75 nl, or the total exposed surface area is 4*$\frac{1}{2}$ BP=0.15 mm$^2$, where P is the height of the isosceles triangle on the pyramid. Assuming a fully-soluble drug has a concentration of 40 mg/ml, and the microneedle patches has 10×10=100 microneedles, the drug loaded on the microneedles is 100*3.75*40 ng=15 ug. In fact, most microneedles have much lower concentrations because a significant portion of the microneedles must be filled with a matrix material to provide the strength for penetration. For drug that is coated on the microneedles' surface, assuming a coating of 10 um and 100 microneedles, the drug volume that is coated on the microneedles is 100*0.01*0.15*40 ng=6 ug. In practice, only a small portion of the coated drugs is released into the skin, a substantial amount of drug will reside on the surface. Although the drug loading capacity of microneedles can be increased by increasing the size or the quantity of the microneedles, it may not be viable to do so in practice. For example, increasing the microneedle size may increase the pain or decrease the dissolution rate of the microneedle. Increasing the quantity of the microneedles inevitably increases the patch size which reduces the penetration effectiveness of the microneedles due to body's curvature.

Figure 1:
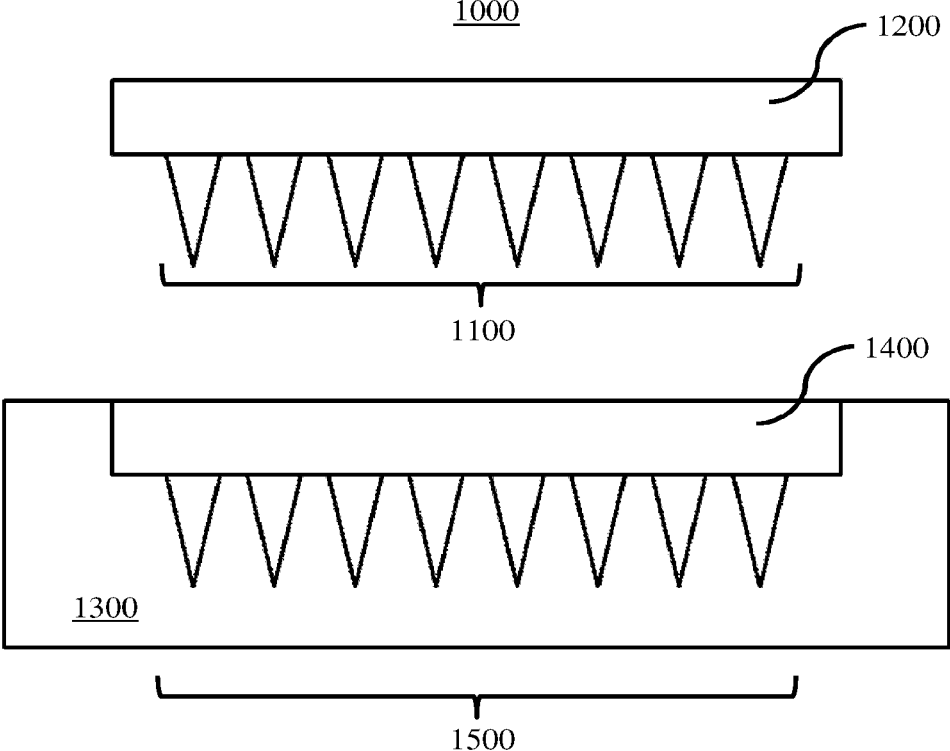
FIG. 1 shows a microneedle patch comprising a substrate and a plurality of microneedles extending from the substrate and a corresponding microneedle template comprising a substrate cavity and a plurality of microneedle cavities.

The second limitation of microneedle technology is drug loading precision. FIG. 1 shows a typical microneedle patch 1000 comprising a plurality of microneedles 1100 and a substrate 1200 and the corresponding microneedle template 1300 comprising a substrate cavity 1400 and a plurality of microneedle cavities 1500. There are 100 pyramid microneedles with height of 500 um and base of 150 um, together having a total volume of 100*3.75 nl=0.375 ul. The substrate is a 1 mm thick 8 mm×8 mm footprint, having a volume of 64 ul. If the microneedle patch 1000 is made from a homogeneous casting solution made of a matrix material and an active ingredient, then the drug loaded into the microneedles is 0.375/64=0.59%. Due to the fact that only the drug in the microneedles will get delivered (which is 0.59%), most of the drug that resides in the substrate is wasted.

Figure 2:
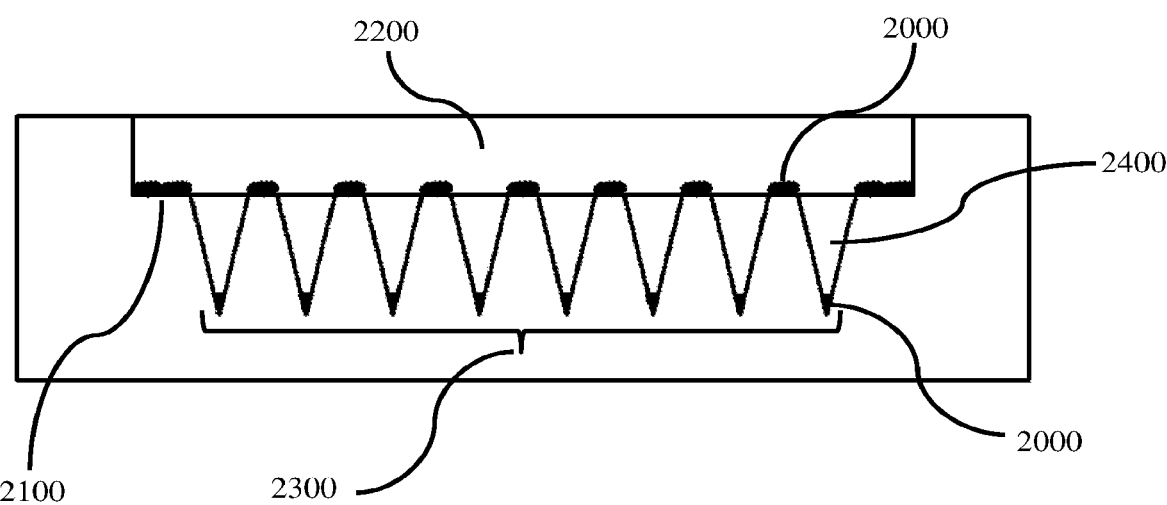
FIG. 2 shows the drug sediment on the bed of substrate cavity and on the tips of microneedle cavities on a normal microneedle template.

To increase the loading precision and reduce drug wastage, PCT application WO2015/122838A1 proposed to employ centrifugal force to sediment the suspended insoluble particles to the bottom of the microneedle template. FIG. 2 shows the drug sedimentation 2000 caused by a centrifugation wherein the insoluble drug particles are pushed to the bed 2100 of the substrate cavity 2200 and the tips 2300 of the microneedle cavities 2400. One benefit of this method is that the drug is concentrated at the tips of the microneedles now, and so long as the microneedles dissolve to a certain height beyond the drug, full drug delivered is achieved. Another benefit is that the drug in the substrate cavity 2200 above the microneedle cavities 2400 is now pushed to the tips of the microneedles due to centrifugation.

Figure 3:
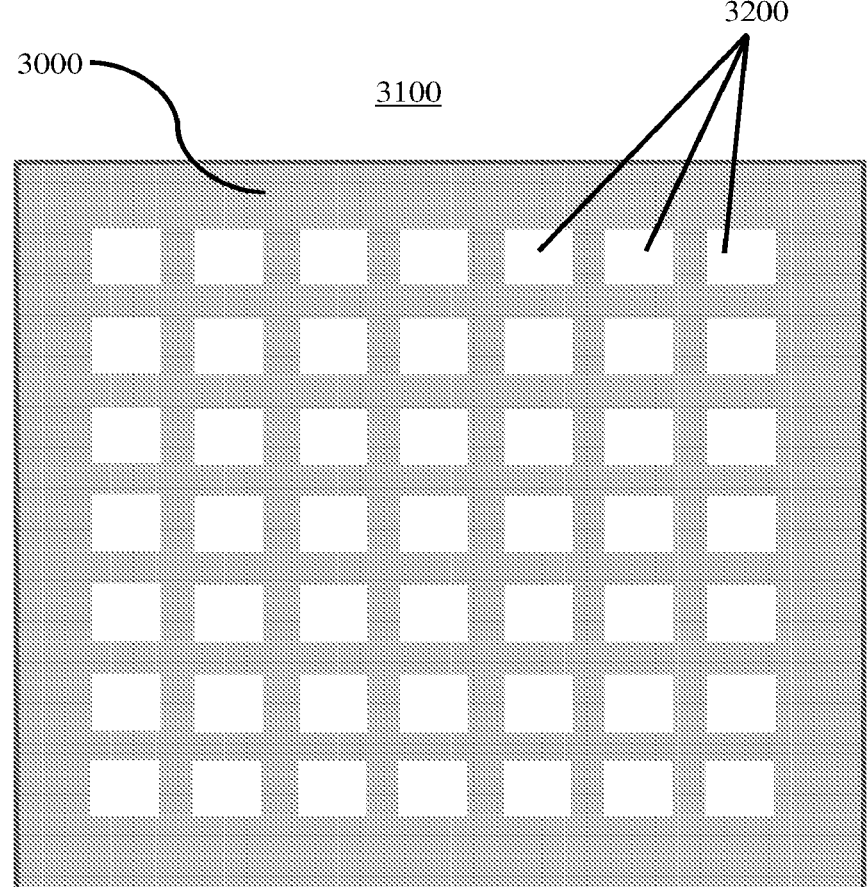
FIG. 3 shows the insoluble drug 3000 which is sedimented on a microneedle template 3100 after centrifugation.

FIG. 3 shows the insoluble drug 3000 which is sedimented on a microneedle template 3100 after centrifugation. The microneedle template 3100 has a substrate area of 8 mm*8 mm=64 mm$^2$. The microneedle template 3100 comprises 14×14 microneedle cavities 3200 of 600 um-height and 200 um-base pyramids. The total area of the microneedle cavities' bases is 14*14*(0.2*0.2)=7.84 mm$^2$, which is about 7.84/64*100%=12.25% of the substrate area.

Figure 4:
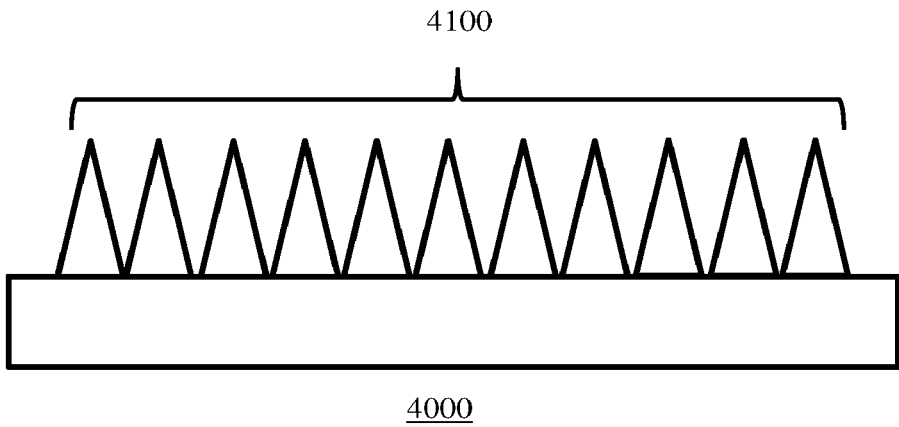
FIG. 4 shows a microneedle patch that has a foot-to-foot microneedle configuration.

The insoluble drug 3000 suspended in the solution is expected to sediment to the bottom after the centrifugation, from which 12.25% will be filled into the microneedle cavities 3200. By using a drug suspension, the drug loading capacity is immediately increased by 10 folds (0.59% increased to 12.25%). It will be apparent that, to increase the drug loading into the microneedles, the microneedles' base area has to be maximized One way to maximize the microneedles' base area is to cramp the microneedles such that the microneedles are standing foot-to-foot, leaving no area between adjacent microneedles. FIG. 4 shows a microneedle template 4000 that has this foot-to-foot microneedle configuration. The microneedle cavities 4100 are adjacent to each other and their peak-to-peak distance is equal to their base dimension. In this foot-to-foot microneedle configuration, the area ratio of the microneedle bases to the substrate is in theory one, so 100% of the sedimented drug will be filled into the microneedles.

However, this microneedle configuration is undesirable from either fabrication point of view or application point of view. From fabrication point of view, such a foot-to-foot microneedle configuration imposes great challenges in the fabrication of the master mould because the cutting tool has to be made so thin that it breaks or wears off very frequently and rapidly during the machining process. From application point of view, the close distance between microneedles' tips reduces the penetration ability of the microneedles due to a 'needle-bed' effect, in which the viscoelasticity of the skin enhances the resistance to the penetration of closely-packed microneedles, causing little or reduced skin penetration.

A Novel Approach to Enhance Drug Loading Capacity of Microneedles

Figure 5:
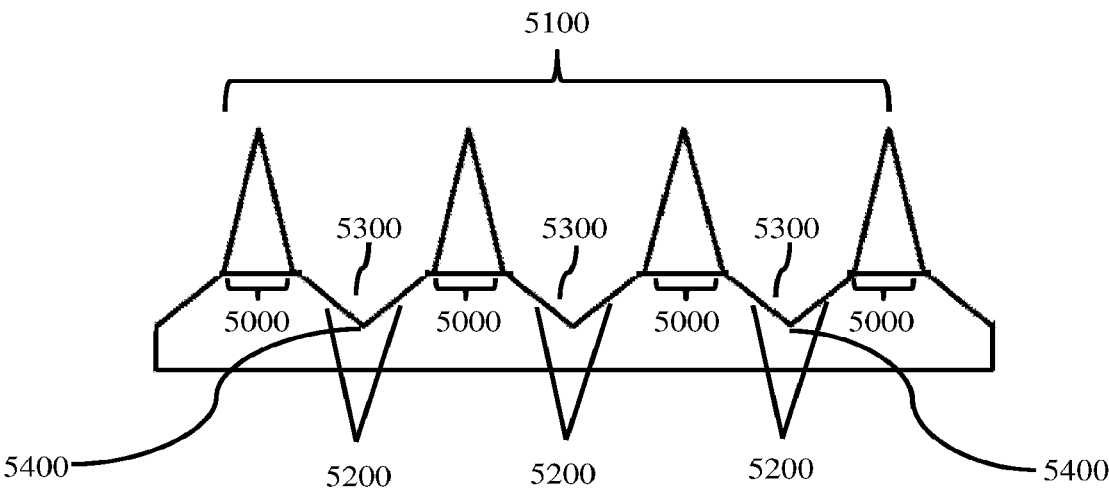
FIG. 5 shows a cross-sectional view of a microneedle master mould whose microneedles have chamfered bases which extend to and adjoin with their neighboring chamfered bases.

An alternative way to maximize the microneedles' base area is to keep the original distance between the microneedles and extend the original base area to the maximum by introducing chamfers at the bases of the microneedles. The base area is maximized when the base area is touching the neighboring base areas. FIG. 5 shows a cross-sectional view of a microneedle master mould whose microneedles have chamfered bases which extend to and adjoin with their neighboring chamfered bases. As shown in the figure, the original bases 5000 of two neighboring microneedles 5100 are extended equally by incorporation of two adjoining but opposite chamfers 5200 spanning the two original microneedle bases 5000. The two adjoining opposite chamfers 5200 form a valley 5300. The bottom point of the valley 5400 is where the opposite chamfers 5200 meet and it is slightly lower than the original bases 5000; the chamfered bases 5400 is at the same level of the bottom point of the valley 5400. Based on the peak-to-peak distance of 500 um and the base dimension of 200 um, the mouth of the valley is 300 um, and the depth of the bottom point of the valley is 50 um-500 um, or more specifically 50 um-200 um. The chamfers can be straight or curved. These characteristics are referred to as the 'chamfered base' features hereinafter.

With the chamfered bases of microneedles, the suspended drug particles will be sedimented into the microneedles, particularly to the tips of the microneedles when the drug particles are subjected to centrifugation, thereby avoiding wasting drugs and increasing drug loading capacity.

Fabrication of the Microneedle Master Mould Comprising 'Chamfered Base' Microneedles The fabrication of microneedle templates comprising chamfered-based microneedle cavities involves a moulding process which requires a master mould that comprises microneedles with a 'chamfered base' feature. This microneedle master mould is the key in fabricating these microneedle templates; once a master mould is provided, the moulding processes that are available are for instance compression moulding, liquid silicone rubber injection moulding or cast moulding. The method of fabricating a master mould has been reported in U.S. Pat. No. 7,497,980B2 awarded to Xu et al. The prior art employed precision wire-cutting, which is an electro-discharge-machining process, to cut through two orthogonal directions for forming pyramidal microneedles on a block of metal.

For incorporating the 'chamfered base' feature, isosceles troughs are incorporated in between the feet of adjacent microneedles by means of physical removal, including grinding, milling, electro-discharge machining, laser machining, and so on. The incorporation of isosceles troughs is done in two orthogonal directions on the surface of a metal block so that four chamfer surfaces are incorporated on each microneedle.

Figure 6A:
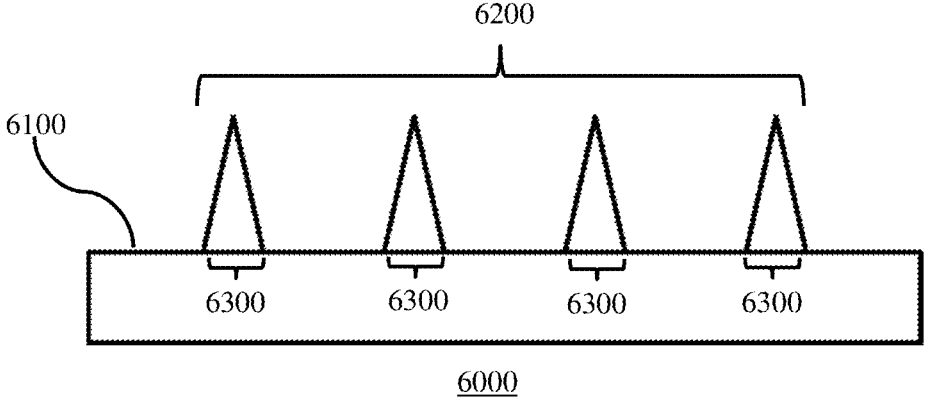
FIG. 6A shows a microneedle master mould made by the prior art
Figure 6B:
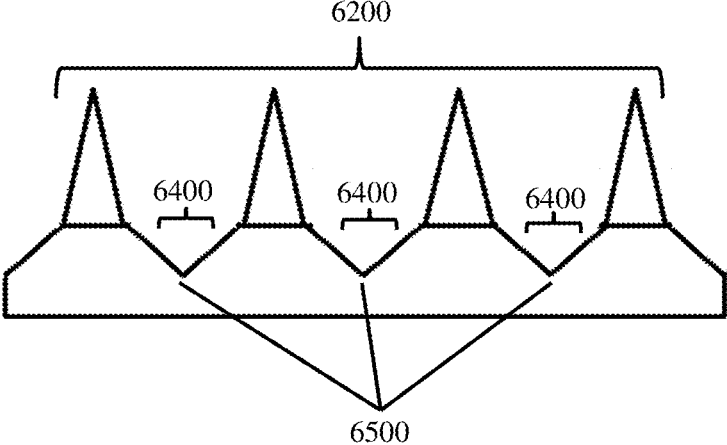
FIG. 6B shows a microneedle master mould incorporated with 'chamfered base' feature.
Figure 7A:
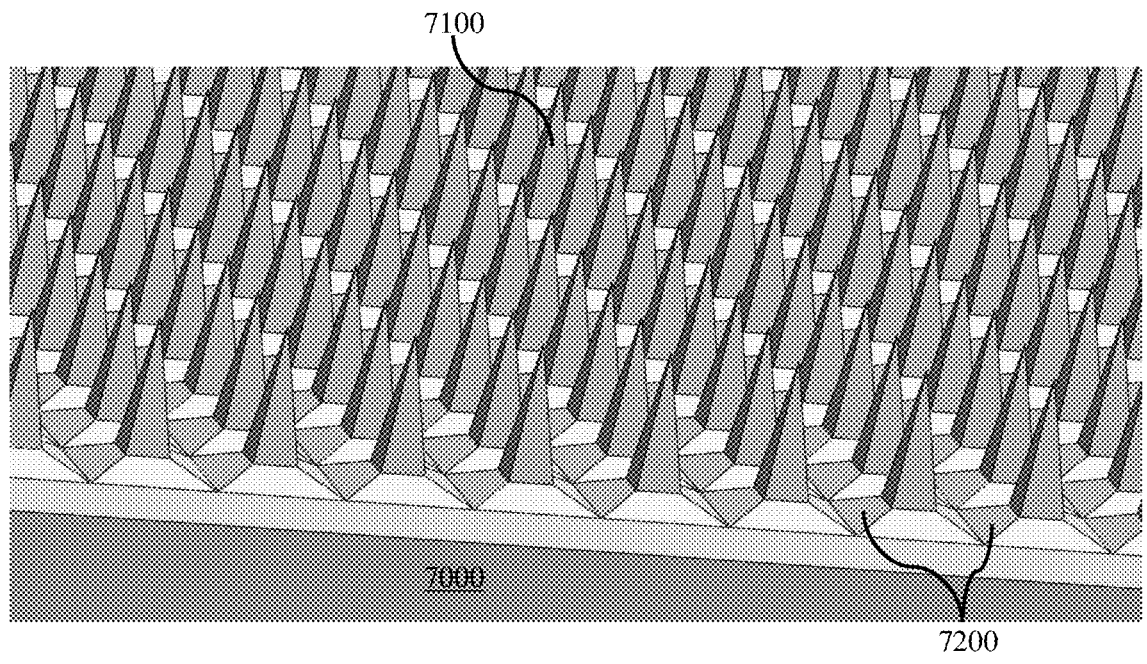
FIG. 7A shows a microneedle master mould 7000 comprising an array of microneedles 7100 wherein each microneedle comprises four straight chamfer surfaces
Figure 7B:
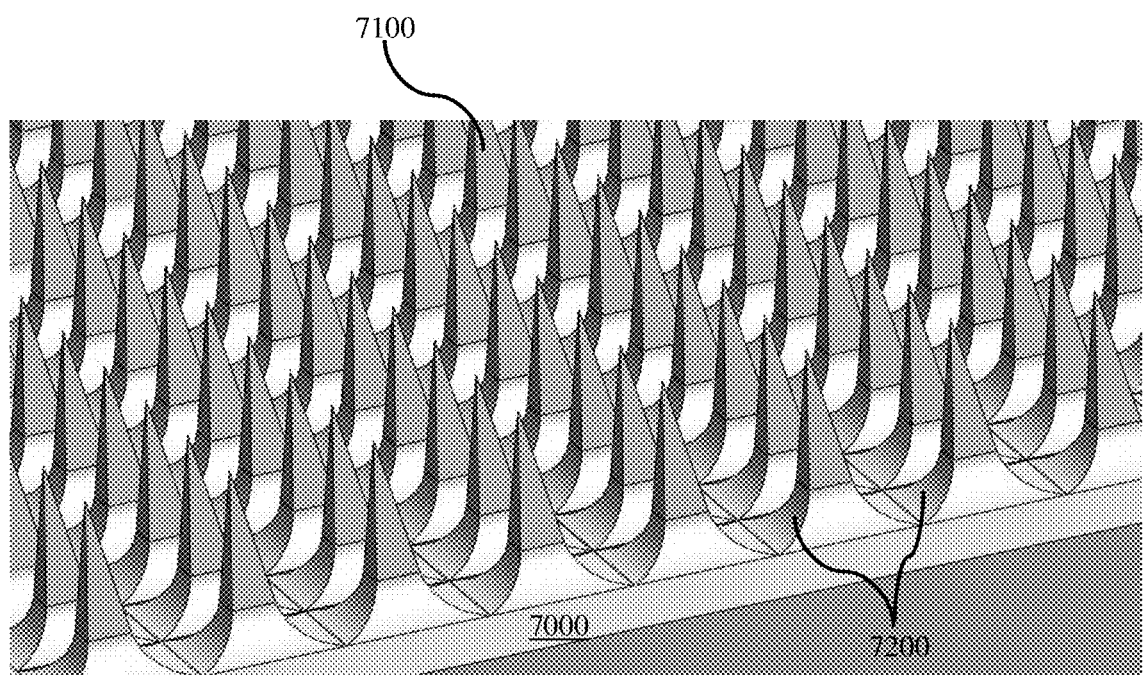
FIG. 7B shows a microneedle master mould 7000 comprising an array of microneedles 7100 wherein each microneedle comprises four curved chamfer surfaces 7200.

FIG. 6 shows (a) a microneedle master mould made by the prior art and (b) a microneedle master mould incorporated with 'chamfered base' feature. In FIG. 6(a), a microneedle master mould 6000 comprises a substrate surface 6100 an array of microneedles 6200 is presented. The array of microneedles 6200 extends from the substrate surface 6100 via their bases 6300. Conventionally the tip-to-tip spacing of the microneedles and a relatively small base dimension will leave a considerable horizontal substrate surface 6100 between two neighboring microneedles. To enhance the drug loading capacity of the microneedles, we propose to maximize the base area without reducing the tip-to-tip spacing, which Can be achieved by cutting isosceles troughs 6400 in between the microneedles 6200 on the microneedle master mould 6000, which is described in the prior art U.S. Pat. No. 7,497,980B2 awarded to Xu et al., as shown in FIG. 6(b). The incorporation of the isosceles troughs is performed in two orthogonal directions on the master mould 6000 to provide all microneedles with the chamfered bases. As mentioned previously, the isosceles trough is a combination of two adjoining opposite chamfer surfaces. The isosceles troughs 6400 have a base that spans from two adjacent microneedles' feet. The isosceles troughs 6400 have a depth that measures from the substrate surface 6100 to the troughs' valleys 6500. Although the isosceles troughs shown in FIG. 6(b) have four straight chamfer surfaces, the troughs' sides are not limited to straight sides. For example, FIG. 7 shows a microneedle master mould 7000 comprising an array of microneedles 7100 wherein each microneedle comprises on their bases four (a) straight chamfer surfaces and (b) curved chamfer surfaces 7200. Once the microneedle master mould is made, the microneedle templates can be moulded by the processes mentioned above.

As shown in FIG. 6(b), the original bases of microneedles has been extended from between the feet of two adjacent microneedles originally to between the valleys 6500 of two adjacent troughs 6400, without changing the tip-to-tip distance and the sharpness of the microneedles. These chamfered bases of the microneedles, which extend to and adjoin with their neighboring chamfered bases, eliminate any horizontal substrate area between microneedles and help collect those sedimented drug particles, which otherwise would land on the horizontal substrate area during centrifugation process, into the microneedles. These features are referred to as 'chamfered base' feature hereinafter. As the centrifugation process will push and pack the sedimented drug particles to the bottom, the sedimented drug particles will fill the microneedles from the tips towards the bases.

Method of Loading Suspended Drug into 'Chamfered Base' Microneedles

The following paragraphs will describe a method of loading a suspended drug into the 'chamfered base' microneedles. Before the fabrication starts, a drug suspension is prepared. A suspension can be made when a solid drug is mixed with water beyond its solubility limit or saturation limit. This is normally achieved with drugs that are mildly soluble in water. For water soluble drugs, including chemicals, proteins and peptides, the drug particles can be made insoluble by encapsulating an insoluble material over the drug particles. The concentration of the drug suspension is related to the specified dose of the microneedle patch and the minimum volume which is required to effectively cover the substrate cavity during the centrifugation process. For example, if the specified dose is 5 mg and the minimum volume to cover the substrate cavity is 400 ul, then the concentration of the drug suspension is 5 mg/400 ul, or 12.5 mg/ml. More water can be used to make a less concentrated suspension, but more volume may lead to spillage during centrifugation process or longer drying time. Similarly, a matrix material solution is prepared. A matrix material is the base material that form microneedles and provide the required physical strength and dissolution characteristics of dissolving microneedles. Some examples of matrix materials for making dissolving microneedles include hyaluronic acid (HA), polyvinylpyrrolidone (PVP), carboxymethyl cellulose (CMC), so on and so forth. The typical concentration of HA, PVP and CMC solution is from 0.3 to 1 g/ml, 0.5 to 2 g/ml, and 0.5 to 1 g/ml respectively. Higher concentration of the matrix material solution provides better strength to the microneedles.

FIG. 8 shows a flow chart that summarizes the steps for making microneedles with enhanced drug loading capacity. Firstly, a microneedle template comprising a substrate cavity and a plurality of 'chamfered base' microneedle cavities is provided. Secondly, the drug suspension is loaded in the substrate cavity on the microneedle template. Thirdly, the loaded microneedle template is subjected to a centrifugation process at 5,000 RPM for 5 minutes.

The drug will be sedimented in the microneedles and the supernatant will remain in the substrate cavity. The supernatant is removed from the substrate cavity of the microneedle template. It is important to note that the substrate cavity is a general term used herein for denoting a space above the microneedle cavities for loading and containing any liquid for making dissolving microneedles. It is commonly understood by the persons skilled in the art that a microneedle template may be made without a substrate cavity but using other external method or parts, for example a two-part mould system, for loading and containing the liquid on the microneedle cavities for fabricating dissolving microneedles. Hence, by substrate cavity herein we mean a space for loading and containing on microneedle cavities any liquid used for making dissolving microneedles, and our meaning shall include a flat microneedle template without a substrate cavity but uses external parts to allow loading and containing of any liquid used for making dissolving microneedles.

Fourthly, the matrix material solution is loaded in the substrate cavity on the microneedle template. Fifthly, the loaded microneedle template is again subjected to a centrifugation process at 5,000 RPM for 7 minutes. The centrifugation will keep the sedimented drug in the microneedle cavities and at the same time force the matrix material solution into the microneedle cavities and encapsulate the drug. The excessive solution will fill the substrate cavity and form the substrate of the microneedles.

Lastly, the centrifuged microneedle template is subjected to a controlled environment for drying. The centrifugation may be continued until the dissolving microneedle patch is dried. This is normally done with a refrigerated centrifuge where the temperature in the centrifuge is controlled at 0-20 degrees Celsius. Alternatively, the centrifuged microneedle template may be removed from the centrifuge machine and then subjected to a controlled environment for drying the microneedle patch. The controlled environment includes a temperature range of 15-30 degrees Celsius, relative humidity range of 30%-50% and under atmospheric pressure.

Example 1

Two types of microneedle templates were prepared, one is normal type of patch size 8 mm×8 mm, 14×14 array, height=600 um, Base=200 um×200 um, and tip-to-tip distance=500 um; and the other is with the same configurations and with the 'chamfered base' feature. The drug suspension was diclofenac sodium with concentration of 2.5 mg/ml. The matrix material solution was hyaluronic acid (HA) 0.6 g/ml. Firstly, 40 ul of diclofenac suspension (containing 0.1 mg diclofenac sodium) was loaded on the two microneedle templates. The loaded templates were subjected to centrifugation of 5,000 RPM for 5 minutes, after which the supernatant was removed from the substrate cavity of the microneedle template. Secondly, 60 ul of HA solution was loaded on the two microneedle templates and subsequently were subjected to centrifugation of 5,000 RPM for 7 minutes. Lastly, the microneedle templates were placed in an environment chamber at 25 degrees Celsius and RH 40% at atmospheric pressure for 8 hours.

Figure 9A:
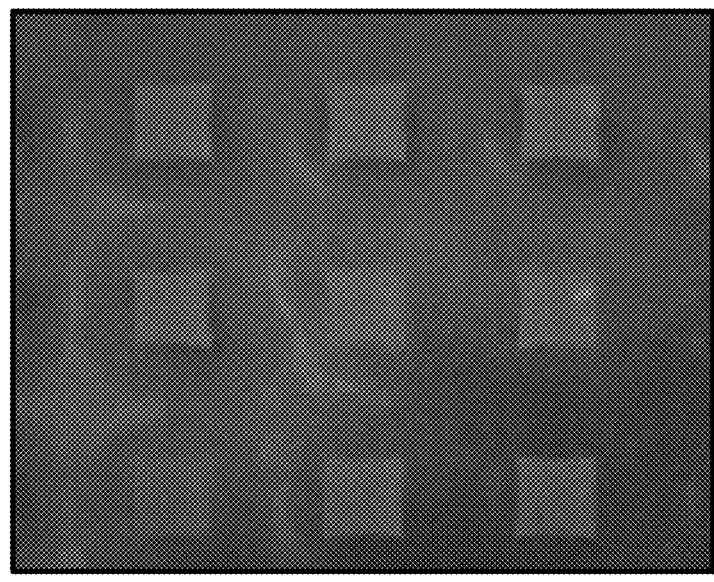
FIG. 9A shows the sedimentation of the diclofenac sodium on the substrate surface of a normal template
Figure 9B:
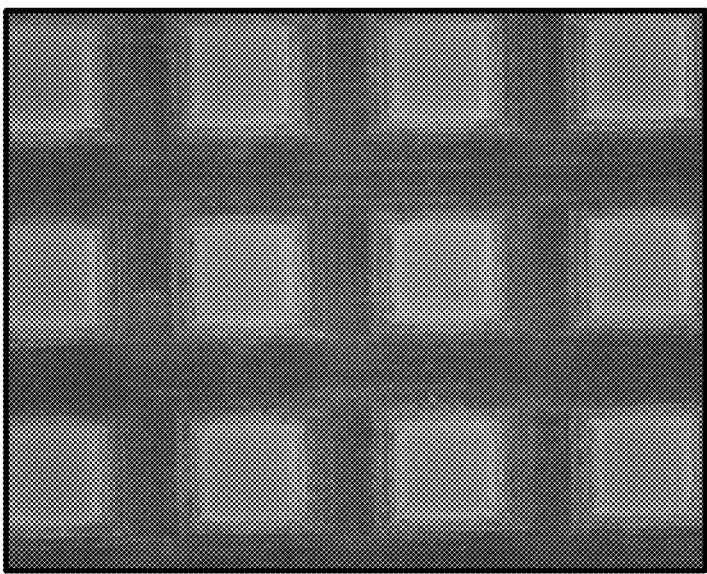
FIG. 9B shows the sedimentation of the diclofenac sodium on the substrate surface of a 'chamfered base' template.

FIG. 9 shows the sedimentation of the diclofenac sodium on the horizontal substrate surface of the (a) normal template and (b) 'chamfered base' template. In FIG. 9(a), it can be clearly seen that the sedimented drug landed on the horizontal substrate surface 9100 of the normal microneedle template 9000 whereas in FIG. 9(b), all drug sedimentation was filled into microneedles. Hence, it is apparent that the wastage of drug is minimized and that the drug loading capacity of the microneedle patches is greatly enhanced.

TABLE 1

| The Averaged Contents of Diclofenac Sodium in Various Specimens | | |
| --- | --- | --- |
| Patch Type | Specimen | Diclofenac Sodium (ug) |
| Normal Patch | A | 99.5 |
| | B | 13.8 |
| | C | 85.7 |
| 'Chamfered Base' Patch | A | 99.8 |
| | B | 97.4 |
| | C | 0.2 |

To confirm the drug loading in the microneedles quantitatively, the normal microneedle patches and the 'chamfered base' microneedle patches which were loaded with 0.1 mg of diclofenac sodium and were subjected to UV absorption measurement. Each type of microneedle patches had specimens A, B and C, where specimen A was the entire microneedles patches, specimen B was the microneedles that were physically removed from the substrates, and specimen C was the substrates without microneedles. The absorption values of the specimens were used to determine the content of diclofenac sodium in the specimens with the help of a standard concentration curve developed in-house. Each specimen had 10 samples and the individual contents were averaged. Table 1 above summarizes the averaged contents of diclofenac sodium in various specimens:

The amount of diclofenac sodium found in the microneedles of the normal patches (13.8 ug) was consistent with our previous theoretical prediction where 12.5% of the drug was expected to be loaded into the microneedles. As for the 'chamfered base' microneedle patches, excellent drug loading (97.4 ug/100 ug, or 97.4%) was found. There were traces amount of diclofenac sodium found in the substrate, which is believed to come from wall adhesion during loading and centrifugation processes. As the drug contents were well within 10% tolerance of acceptable dosing range, the present approach is validated as an excellent process in making drug-laden dissolving microneedles.

Example 2

This experiment was conducted to study the significance of the centrifugation order of the drug suspension and the matrix material solution. A 'chamfered base' microneedle template with configurations 10×10 array, height=600 um, base=200 um×200 um, tip-to-tip distance=500 um, was used. The drug suspension was diclofenac sodium at concentration 25 mg/ml and the matrix material solution was sodium hyaluronate (HA) at concentration 0.6 g/ml. there were two specimens, one was 'Matrix First' and the other was 'Drug First'. For 'Matrix First' specimens, 40 ul of the matrix material solution was loaded on the microneedle template and the loaded template was subjected to centrifugation of 5,000 RPM for 5 minutes. Subsequently, 40 ul of drug suspension was loaded on the HA-filled microneedle template. The microneedle template was subjected another centrifugation of 5000 RPM for seven minutes. Finally, the centrifuged template was observed under a stereo microscope. For the 'Drug First' specimens, the loading and centrifugation order was reversed.

Table 2 below shows the analysis of diclofenac sodium content in the specimens 'Drug first' and 'Matrix First'. The results show that there was significant portion of drug which remained in the substrate. The 'Drug First' specimens had 95.7% drug loading efficiency while the 'Matrix First' specimens had only 67.1% drug loading efficiency. This may be due to the viscoelastic property of the HA which prevented the drug particles from entering the tiny microneedle cavities. This is a microfluidic phenomenon where the viscous force dominates the inertial force when the physical dimensions become microscale. On the other hand, the drug suspension is a water solution and does not possess the same viscoelastic property that HA solution exhibits. Hence, by separating the loading and centrifugation step of the drug suspension and the matrix material solution, the drug loading capacity is greatly enhanced.

TABLE 2

| Drug Loading Efficiencies Due to Different Loading Orders | | |
|---|---|---|
| Patch Type | Specimen | Diclofenac Sodium (ug) |
| Drug First | A | 99.3 |
| | B | 95.7 |
| | C | 0.3 |
| Matrix First | A | 99.6 |
| | B | 67.1 |
| | C | 29.4 |

What is claimed is:

1. A method of manufacturing dissolving microneedles, the method comprising:
   a. Providing a microneedle template, the microneedle template comprising a plurality of pyramidal microneedle cavities, immediately under each pyramidal microneedle cavity is incorporated with a chamfered base which extends to and adjoins with its neighboring chamfered bases, wherein the extending and adjoining of the chamfered bases eliminates any horizontal substrate area between the microneedle cavities,
   b. Preparing a suspension made of a drug and loading the template with said suspension,
   c. Centrifuging the loaded microneedle template to fill the microneedle cavities with the drug suspension, and causing the drug suspension to completely settle to the bottom of the microneedle cavities,
   d. Loading a matrix material solution on the template, and
   e. Centrifuging the loaded microneedle template to fill the microneedle cavities with the matrix material solution.

2. The method for manufacturing dissolving microneedles according to claim 1, wherein in step c, the loaded microneedle template is subjected to a centrifugation process at 5000 rpm for 5 minutes.

3. The method of manufacturing dissolving microneedles according to claim 1, further comprising a drying step that places the microneedle template in a controlled environment for drying.

4. The method of manufacturing dissolving microneedles of claim 3, wherein the controlled environment for drying involves centrifugation.

5. The method of manufacturing dissolving microneedles according to claim 1, wherein the drug suspension comprises insoluble drug particles in water.

6. The method for manufacturing dissolving microneedles according to claim 1, wherein the matrix material is made of sodium hyaluronate, polyvinylpyrrolidone, carboxymethyl cellulose or any combination thereof.

7. The method of manufacturing dissolving microneedles of claim 3, wherein the controlled environment involves a temperature range of 15-30 degrees Celsius, a relative humidity range of 30%-50% at atmospheric pressure.

8. The method of claim 4, wherein the centrifugation is performed in a temperature range of 0-20 degrees Celsius.

9. The method of manufacturing dissolving microneedles according to claim 1, wherein the microneedle template is made of an elastomeric material.

10. The method of manufacturing dissolving microneedles according to claim 1, wherein the microneedle template is made of silicon material.

11. The method of claim 1, wherein the chamfered base of the pyramidal microneedle cavities is made of a straight surface.

12. The method of claim 1, wherein the chamfered base of the pyramidal microneedle cavities is made of a curved surface.

13. A microneedle master mold for manufacturing the microneedle template of claim 1, comprising:
   a. a metal base,
   b. a plurality of pyramidal microneedles, the plurality of pyramidal microneedles is formed by engraving on the surface of the metal base,
   c. a plurality of isosceles throughs, wherein one isosceles through is engraved between the feet of two adjacent pyramidal microneedles, the isosceles troughs surrounding each pyramidal microneedle forming a chamfered base immediately under each pyramidal microneedle thereby eliminating the horizontal substrate area between the adjacent microneedles.

14. The microneedle master of claim 13, wherein the chamfered base is made of a straight surface.

15. The microneedle master of claim 13, wherein the chamfered base is made of a curved surface.

16. The microneedle master mold according to claim 13, wherein the size of the isosceles trough is: the base of the isosceles trough is 300 m, and the depth of the isosceles trough is 50 m-500 m.

17. The microneedle master mold of claim 16, wherein the depth of the isosceles trough is 50 μm-200 μm.

18. A method for making the microneedle master mold of claim 13,
   a. First, a plurality of pyramidal microneedles is carved on the surface of a metal block;
   b. Then, one isosceles trough is carved between the feet of the adjacent pyramidal microneedles; the method of carving the isosceles grooves involves conventional physical removal process such as grinding, milling, electro-discharge machining, laser machining steps;

Wherein the isosceles troughs are carved in two orthogonal directions on the surface of the metal block, thereby incorporating four chamfered surfaces immediately under each pyramidal microneedle to eliminate the horizontal substrate area between the adjacent microneedles.

19. The method of claim 18, wherein the size of the isosceles trough is: the base of the isosceles trough is 300 μm, and the depth of the isosceles trough is 50 μm-500 μm.

20. The method of claim 19, wherein the depth of the isosceles trough is 50 μm-200 μm.

\* \* \* \* \*